(12) United States Patent
Doniat et al.

(10) Patent No.: US 8,191,397 B2
(45) Date of Patent: Jun. 5, 2012

(54) METHODS FOR CHECKING AND CALIBRATING CONCENTRATION SENSORS IN A SEMICONDUCTOR PROCESSING CHAMBER

(75) Inventors: Francois Doniat, Wilmington, DE (US); Ronald S. Inman, Brookfield, IL (US); Nathan Stafford, Wilmington, DE (US); Axel Soulet, Berkeley, CA (US); Jean-Louis Marc, La Redorte (FR)

(73) Assignees: Air Liquide Electronics U.S. LP, Dallas, TX (US); American Air Liquide, Inc., Fremont, CA (US)

( * ) Notice: Subject to any disclaimer, the term of this patent is extended or adjusted under 35 U.S.C. 154(b) by 729 days.

(21) Appl. No.: 12/332,796

(22) Filed: Dec. 11, 2008

(65) Prior Publication Data
US 2009/0151419 A1   Jun. 18, 2009

Related U.S. Application Data

(60) Provisional application No. 61/013,142, filed on Dec. 12, 2007.

(51) Int. Cl.
*G01N 21/00* (2006.01)
(52) U.S. Cl. .......................................................... 73/1.03
(58) Field of Classification Search ................ 73/1.03; 366/152.4
See application file for complete search history.

(56) References Cited

U.S. PATENT DOCUMENTS

| 6,296,711 | B1 | 10/2001 | Loan et al. |
| 6,799,883 | B1* | 10/2004 | Urquhart et al. ........... 366/152.4 |
| 7,195,026 | B2 | 3/2007 | Znamensky et al. |
| 2003/0101795 | A1* | 6/2003 | Makihara et al. .............. 73/23.2 |
| 2009/0090164 | A1 | 4/2009 | Inman |

OTHER PUBLICATIONS

"Chemical Delivery Manifold With a Fluid Monitoring Sensor", Publication No. IPCOM000124353D, http://www.ip.com.

* cited by examiner

*Primary Examiner* — Hezron E Williams
*Assistant Examiner* — Tamiko Bellamy
(74) *Attorney, Agent, or Firm* — Patricia E. McQueeney

(57) ABSTRACT

The present invention provides methods for checking and calibrating one or more concentration sensors in an open or closed system. More specifically, in one embodiment of the present invention, the disclosed method allows for the checking and calibration of one or more concentration sensors in which removal of the liquid from the system is required. In two additional embodiments, the disclosed methods allow for the checking and calibration of one or more concentration sensors without having to remove the liquid from the closed system thereby minimizing contamination of the system while at the same time greatly reducing or eliminating contact of the user with the liquid.

10 Claims, 4 Drawing Sheets

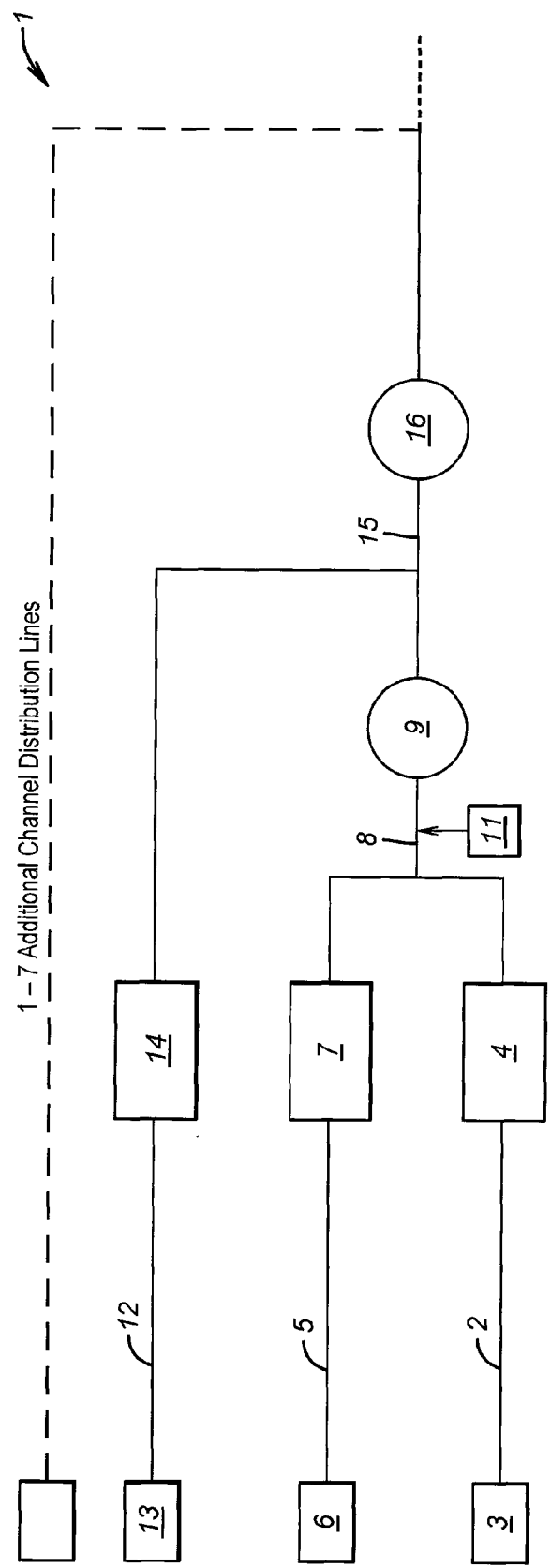

METHODS FOR CHECKING AND CALIBRATING CONCENTRATION SENSORS IN A SEMICONDUCTOR PROCESSING CHAMBER

CROSS REFERENCE TO RELATED APPLICATIONS

The present application claims the benefit of U.S. Provisional Application Ser. No. 61/013,142, filed Dec. 12, 2007, herein incorporated by reference in its entirety for all purposes.

FIELD OF THE INVENTION

The present invention relates to methods for checking and calibrating one or more concentration sensors that are used in a system for delivering blends of liquids to a semiconductor processing chamber. More specifically, the present invention relates to methods for checking a concentration sensor and for calibrating the concentration sensor while at the same time maintaining the liquids in either a closed system or an open system.

BACKGROUND OF THE INVENTION

As electronic devices and the integrated circuits evolve and become more complex, the manufacturing processes which produce these semiconductor devices must also evolve. Numerous chemical components are utilized in the production of a single integrated circuit, all of which need to be provided and distributed within the semiconductor manufacturing facility. Liquid distribution systems take the required liquid chemicals from their storage point, and provide them to the end point of use, which is often the semiconductor processing tool.

One factor to successful semiconductor manufacture is the maintenance of the liquids being distributed. The concentration of the liquids distributed is often a critical aspect of the processes utilized for semiconductor manufacture. Accordingly, it is essential that the concentration of the liquids utilized in the distribution system be correct. One method for checking the accuracy of the concentration utilized is through concentration sensors which allow for the monitoring if the concentrations of the liquids that pass therethrough. As is the case with most sensors, these concentration sensors must be periodically checked and calibrated to ensure that they function properly.

Consequently, there exists a need for one or more methods to determine if there is a need to calibrate the concentration sensors in both closed systems and open systems.

SUMMARY OF THE INVENTION

The present invention provides methods for checking and calibrating one or more concentration sensors in an open or closed system. More specifically, in one embodiment of the present invention, the disclosed method allows for the checking and calibration of one or more concentration sensors in which removal of the liquid from the system is required. In two additional embodiments, the disclosed methods allow for the checking and calibration of one or more concentration sensors without having to remove the liquid from the closed system thereby minimizing contamination of the system while at the same time greatly reducing or eliminating contact of the user with the liquid.

BRIEF DESCRIPTION OF THE FIGURES

FIG. 1C provides a schematic of the second process embodiment.

DETAILED DESCRIPTION OF THE INVENTION

Figure 1A:
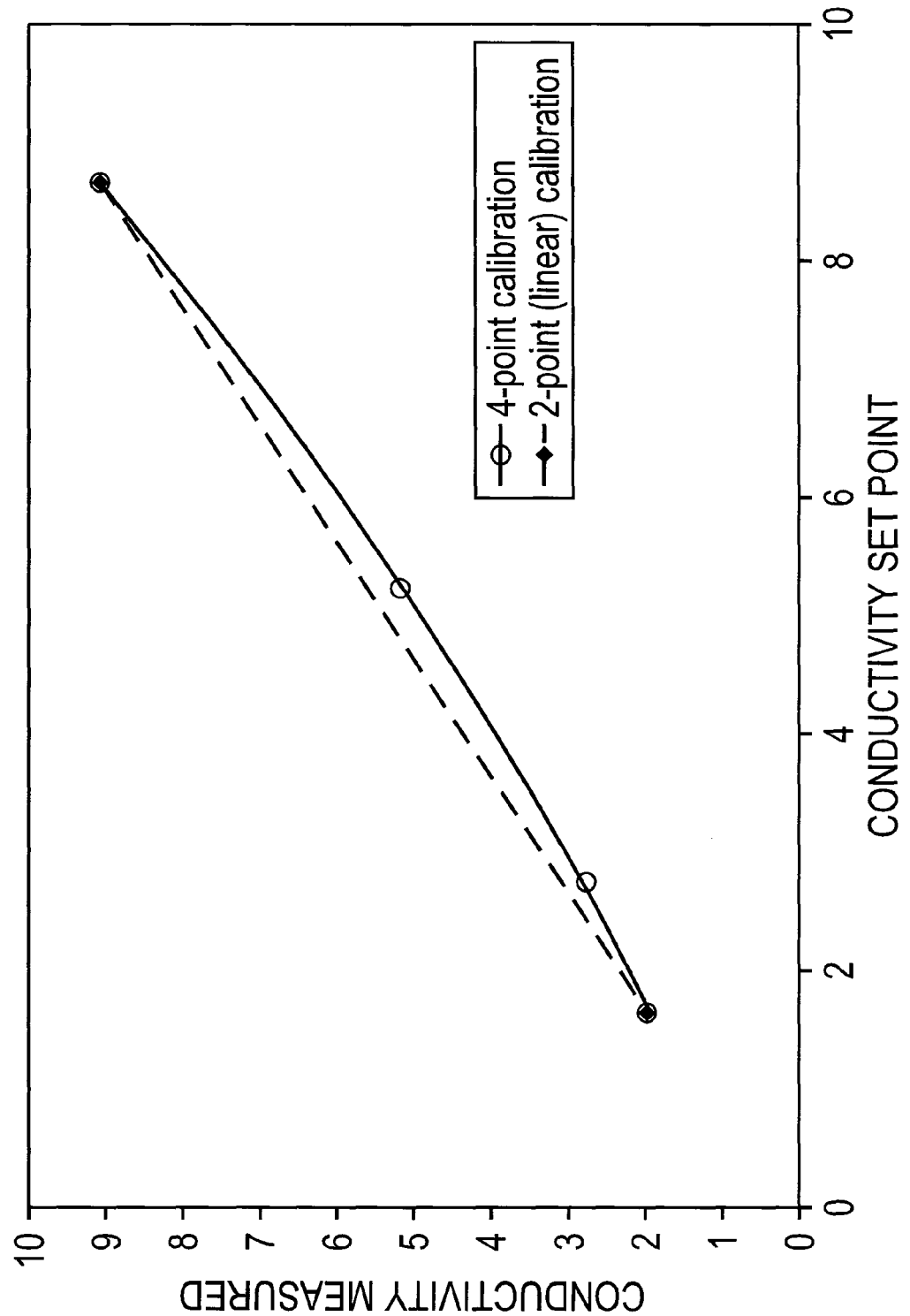
FIG. 1A provides a graph of the comparison of a two point calibration versus a four point calibration using a conductivity sensor.

The present invention provides for the checking and calibrating of one or more concentration sensors in a liquid distribution system. More specifically, the methods of the present invention provide for the checking and calibrating of one or more concentration sensors in a liquid distribution system for semiconductor manufacture. Note that while the preferred embodiments of the present invention are meant to be applicable with regard to semiconductor manufacture, those of ordinary skill in the art will recognize that such methods may also be utilized with regard to the checking and/or calibration of concentration sensors in any application which requires the use of a liquid distribution system such as that described herein.

The liquid distribution system for each embodiment of the present invention may comprise two or more chemical distribution lines. As used herein, the phrase "liquid distribution system" refers to the structural arrangement of the system, including any programmable logic controller (PLC) or associated automation when present, whose objective is to deliver a chemical in liquid form from a source to a point of use. The chemical distribution lines may be made of a variety of different types of materials such as stainless steel, polypropylene, polyvinylchloride, Teflon and the like. The only limitation with regard to the type of material utilized is that the material must not decompose or react with the chemicals that flow through the chemical distribution lines. While the liquid distribution system of the present invention may include any number of chemical distribution lines, typically, the liquid distribution system will comprise from two to ten chemical distribution lines in the liquid distribution system, in many instances from two to five chemical distribution lines.

Each chemical distribution line contained in the liquid distribution system of the present invention will include a chemical supply source that houses a chemical in liquid form (a supply source). With regard to all of the embodiments of the present invention, the chemical flows from its chemical supply source throughout the liquid distribution system. In order to assist this flow, each chemical distribution line also includes a flow control device downstream from the chemical supply source which allows for the distribution of the chemical throughout the system at a particular rate. Flow rates of the liquid in the liquid distribution system may vary, but generally will range from about 10 milliliters/minute to about 50 liters/minute, preferably from about 100 millimeters/minute to about 25 liters/minute. The chemical supply source can be a large volume or bulk chemical supply source that is located some distance from the ultimate point of use for the chemical (such as for example a holding tank in a nearby room) or a smaller total volume of chemical located closer to the point of use (such as for example a small cylinder in the same room where the chemical is to be used). As the liquid chemical flows through the liquid distribution system, the flow control device monitors the liquid chemical, and when necessary controls/adjusts the fluid rate. The flow control device utilized may be any conventional flow control device known in the art such as for example an Entegris NIT 6500 type flow control device (commercially available from Entegris).

The chemicals that are housed in the chemical supply sources and distributed throughout the liquid distribution system will depend upon the exact downstream process being practiced. Non-limiting examples of the chemicals that are typically utilized in semiconductor manufacture that would be utilized in a liquid distribution system such as that of the present invention include, but are not limited to, deionized water, $HNO_3$ (nitric acid), $H_2O_2$ (hydrogen peroxide), $NE_4OH$ (ammonium hydroxide), $H_2SO_4$ (sulphuric acid), HF (hydrofluoric acid), HCl (hydrochloric acid), TMAH (tetramethyl ammonium hydrochloride), copper sulphate solutions, and various surfactants as well as chemical blends that include one or more of the same. While deionized water is not per se considered a chemical, deionized water shall be considered a chemical for the purpose of defining the materials that are housed in the chemical supply sources and distributed throughout the liquid distribution system of the present invention. Those of ordinary skill in the art will recognize that if the present methods and system are utilized in other applications besides semiconductor manufacture, that other liquid chemicals will likely be included in this list.

In addition, depending upon the number of chemical distribution lines present, while the same chemical may be included in more than one of the chemical supply sources, those of ordinary skill in the art will recognize that while considered within the broad scope of the present invention, this would not likely be the optimal use of the liquid distribution system. Accordingly, each liquid supply source will in most instances preferably include a different chemical from that housed in the other liquid supply sources (a different chemical housed in each chemical supply source).

In one configuration of the present invention, the liquid distribution system will include a first chemical distribution line which includes a first chemical supply source that houses a first chemical and a first flow control device and a second chemical distribution line which includes a second chemical supply source that houses a second chemical that differs from the first chemical and a second flow control device. In this particular embodiment, the first chemical distribution line and the second chemical distribution line come together to form a first blended chemical distribution line. By virtue of the two chemical distribution lines coming together, it is possible to have a blend of the first chemical and the second chemical which will be further distributed along the liquid distribution system. The ratio of the first chemical to the second chemical will depend upon the set flow rates for the flow control devices. For example, in a situation where the flow rate for the first chemical is set for 50 milliliters/minute and the flow rate for the second chemical is set for 100 milliliters/minute, the volumetric ratio of the first chemical to the second chemical will be 1:2, or in other words, for each part of first chemical present, two parts of the second chemical will be present.

Along this first blended chemical distribution line, downstream from the point where the first chemical distribution line and the second chemical distribution line come together to form the blended chemical distribution line, a first concentration sensor is disposed along the first blended chemical distribution line. The concentration sensor response to the chemical blend that flows through the liquid distribution system is measured by the concentration sensors of the present invention. As used herein, the term "concentration" when used with regard to the sensors of the present invention refers to any quantifiable measurement that can be recorded by the sensor including, but not limited to, optical, electrical, sonic or physical measurements. The concentration sensors utilized in the present invention may be selected from any variety of different types of conventional concentration sensors including, but not limited to, refractive index sensors, infrared light absorbent sensors, UV light sensors, conductivity sensors, ultrasonic sound sensors, and the like. While the concentration sensors utilized in the processes of the present invention may be any type of concentration sensor, in all of the processes of the present invention, the concentration sensors are preferably conductivity sensors. These conductivity sensors preferably provide a conductivity value measured in Siemens/cm. Such conventional concentration sensors are known in the art and are commercially available from a variety of commercially sources such as for example Yokogawa, Hach and Endress & Hauser. Since the accuracy of the chemical blends utilized particularly in semiconductor manufacture is a critical aspect of the manufacture, it is very important that the concentration of the chemical blends be correct. This concentration sensor allows for the monitoring of the concentration of the blend of the first and second chemical. Therefore, as the liquid chemical blend flows through the liquid distribution system, the concentration sensor monitors the concentration of the liquid chemical blend, thereby providing notice to the manufacturer when the chemical blend does not meet the required specifications (specific concentration at a particular temperature).

While any of the sensors noted above may be adjusted manually, they may also be utilized in a manner such that a concentration sensor communicates with a controller. Accordingly, automation of the entire calibration method is possible and to this end a conventional type controller, such as a programmable logic controller may be used. Such controllers may be for example a CPU315-2DP type controller, as manufactured by Siemens. Generally, the programmable logic controller is capable of both sending and receiving signals, such as 4-20 mA, or 0-10 volt type signals. Therefore, the programmable logic controller may receive signals from the concentration sensors (such as readings of the concentration) and may also send out signals such as the signals to adjust the readings of the concentration sensor and the flow control devices when used. The programmable logic controller can be used to calculate whether or not calibration of the concentration sensor is necessary by comparing the concentration sensor response obtained with the established models as further discussed hereinafter which may be downloaded to the controller. A user interface, such as a conventional graphical user interface (e.g. a computer monitor) is provided, and a signal indicative of the comparison may be sent to the user interface by the controller. The programmable logic controller may also be used to automatically "calibrate" the concentration sensor by adjusting the readings/response obtained from the concentration sensors as further discussed hereinafter. The programmable logic controller may also be used in other manners such as by checking and calibrating the flow control devices of the first process embodiment of the present invention.

Calibration is normally carried out in two points, the low and high calibration points, respectively. Therefore, most programmable logic controllers have this limit of two points of calibration. If the two points of measurements are spread too far apart, the assumption of linear response of the sensor together with the programmable logic controller, becomes less correct. If the measurements are then performed in the middle range, or not close enough to the calibration points, the accuracy becomes poor. In the present invention, the use of the programmable logic controller to manage the steps of recording, treating and calibrating the sensor response is a major contributor to the accuracy of the measurements because it allows a multipoint calibration. This way it covers the whole range of concentration targeted, and can apply a non-linear correction factor to compensate the non linearity of the sensor over the large range of measurement. This is further demonstrated in FIG. 1A which provides a graph of the comparison of a two point calibration versus a four point calibration using a conductivity sensor. As can be seen from FIG. 1A, in the case of two point calibration over a large range of concentration (i.e., conductivity), a large error is observed for any points measured in the intermediate range (e.g., 5 mS/cm) on the graph. If a four point calibration is performed, then it is possible to correct for the non-linearity response of the sensor plus controller resulting in an increase of the accuracy. This can be further seen in the following Table 1:

|                              | Two point calibration   |                | Four point calibration  |                |
|------------------------------|-------------------------|----------------|-------------------------|----------------|
| Concentration (wt %) expected | Concentration obtained  | Error (rel. %) | Concentration obtained  | Error (rel. %) |
| 0.0565                       | 0.0568                  | 0.5651         | 0.0569                  | 0.7422         |
| 0.2822                       | 0.2770                  | −1.4586        | 0.2838                  | 0.9605         |
| 0.5809                       | 0.5950                  | 2.4195         | 0.5860                  | 0.8703         |
| 1.1054                       | 1.1107                  | 0.4788         | 1.1089                  | 0.3160         |

The table shows the accuracy improvement in the case of a two point calibration compared to a four point calibration. In both calibration methods, accuracies are below 1% relative because the calibration is performed at concentrations close to the calibration points. At intermediate concentrations, the accuracy is worse in the case of two point calibration. It remains below 1% relative if additional calibration points are added in the medium range.

In a second configuration of the present invention, the liquid distribution system will include a first chemical distribution line which includes a first chemical supply source that houses a first chemical, and a first flow control device, a second chemical distribution line which includes a second chemical supply source that houses a second chemical that differs from the first chemical, and a second flow control device, and a third chemical distribution line which includes a third chemical supply source that houses a third chemical that differs from the first and second chemicals, and a third flow control device. With regard to this configuration, the third chemical distribution line comes together with the first blended chemical distribution line downstream from the first concentration sensor to form a second blended chemical distribution line. Downstream from where the third chemical distribution line comes together with the first blended chemical distribution line, a second concentration sensor, as described hereinbefore, is disposed along this second blended chemical distribution line. This second concentration sensor allows for the monitoring of the concentration of either a blend of the first and second chemical, a blend of the first and third chemical, a blend of the second and third chemical or a blend of the first, second and third chemical. This configuration may also include the controller as discussed hereinbefore.

In a still further configuration of the present invention, the liquid distribution system will include up to ten chemical distribution lines with each chemical distribution line including a chemical supply source that houses a chemical that differs from the chemicals utilized in each of the other chemical distribution lines. In addition, each chemical distribution line will include a flow control device disposed along each chemical distribution line to allow for the adjusting of the flow rate of each chemical throughout the liquid distribution system. As described above with regard to the first configuration, the first chemical distribution line will come together with the second chemical distribution line to form a first blended chemical distribution line which will have disposed thereon, downstream from where the chemical distribution lines comes together, a concentration sensor for monitoring the concentration of the blend of chemicals from the chemical distribution lines. In addition, as noted hereinbefore with regard to the blends, the ratio of the chemicals to one another in the blend can be adjusted based on the flow rate with regard to the associated chemical distribution line of the particular chemical. Each additional chemical distribution line thereafter (with regard to this example chemical distribution lines three to ten) will come together with the preceding blended chemical distribution line downstream from the concentration sensor located on that particular blended chemical distribution line to form an additional blended chemical distribution line. For example, the third chemical distribution line will come together with the first blended chemical distribution line to form a second blended chemical distribution line, the fourth chemical distribution line will come together with the second blended chemical distribution line to form the third blended chemical distribution line, the fifth chemical distribution line will come together with the third blended chemical distribution line to form a fourth blended chemical distribution line and so on. A concentration sensor is disposed along each of the blended chemical distribution lines downstream from where the preceding chemical distribution line comes together with the preceding blended chemical distribution line. Accordingly, the concentration sensors to be calibrated will depend in part upon the chemical blend utilized in the downstream process. A liquid distribution system having up to ten chemical distribution lines would allow for the blending of a variety of chemical blends having anywhere from two to ten different chemicals. For example, if three chemicals are blended—the first chemical from the first chemical supply source, the third chemical from the third chemical supply source and the fifth chemical from the fifth chemical supply source—the second concentration sensor and the fourth concentration source would be checked and calibrated (the second concentration sensor being positioned along the second blended chemical distribution line and the fourth concentration sensor being positioned along the fourth blended chemical distribution line). This configuration may also include the controller as discussed hereinbefore.

In addition to the concentration sensor located along each of the blended chemical distribution lines (blended chemical distribution lines one to nine), there may be disposed thereon, downstream from the associated concentration sensor, an additional concentration sensor disposed on the blended chemical distribution line which will serve as a secondary concentration sensor to validate the readings of the primary concentration sensor. While not necessarily critical to the invention, such secondary concentration sensors will serve as a backup check in the event of failure of the primary concentration sensor.

The chemical distribution system may also include a further means to inject a baseline fluid. As used herein, the term "baseline" refers to the fluid that when flowed through the particular concentration sensor used, provides a concentration sensor response (reading) that is in effect equivalent to zero in that particular sensor. While as noted below, the baseline fluid utilized for establishing a baseline calibration reading for the concentration sensors may be injected via any of the chemical distribution lines (taking into account that the chemical distribution line utilized is far enough upstream to flow the baseline fluid through the particular sensor to be checked and calibrated), there may also be provided in the liquid distribution system an alternative line specifically for injecting the baseline fluid in order to establish a baseline calibration reading in the noted concentration sensor. In one particular embodiment, the alternative line would be positioned in close proximity and prior to the first concentration sensor and could therefore be utilized for the checking and calibrating of all of the downstream concentration sensors in the liquid distribution system. In an alternative embodiment, each concentration sensor could have associated therewith an alternative line which would allow for the injection of a baseline fluid just prior to the concentration sensor to be checked and calibrated. In addition, with regard to each of these embodiments, the alternative line may include a three way valve which would allow for the injection of different baseline fluids at different times.

The baseline fluid utilized depends to some degree upon the method utilized for checking and calibrating the concentration sensor. In addition, those of ordinary skill in the art will also recognize that the baseline fluid for the present methods will depend upon the actual sensor used. Typically, the baseline fluid will be selected from one or more of inorganic compounds such as deionized water, gas such as nitrogen gas or air, organic solvents such as ethylene glycol or toluene, and other types of organic solvents which would be considered as inert for the purposes of this invention. For example, when the concentration sensor is a conductivity sensor, the baseline fluid may be any of the aforementioned baseline fluids. However, when the particular sensor is a refractive index sensor, preferably the baseline fluid is deionized water. Note that while deionized water is included in the definition of a chemical for the purposes of this invention, it may also function as a baseline fluid for establishing a baseline calibration reading for the concentration sensors. Those of ordinary skill in the art will note that this list of baseline fluids is not meant to be exhaustive and that other baseline fluids may be used to accomplish the same objective as the baseline fluids listed above.

The present invention comprises three different process embodiments for checking and calibrating one or more concentration sensors in a liquid distribution system. Two of the process embodiments of the present invention involve the checking and calibration of one or more concentration sensors in a closed system while the remaining process embodiment of the present invention involves the checking and calibration of one or more concentration sensors in an open system. All of the process embodiments of the present invention will typically be carried out at a temperature that ranges from about 15° C. to about 100° C., with the preferred temperature range being from about 25° C. to about 85° C.

First Process Embodiment

Figure 1B:
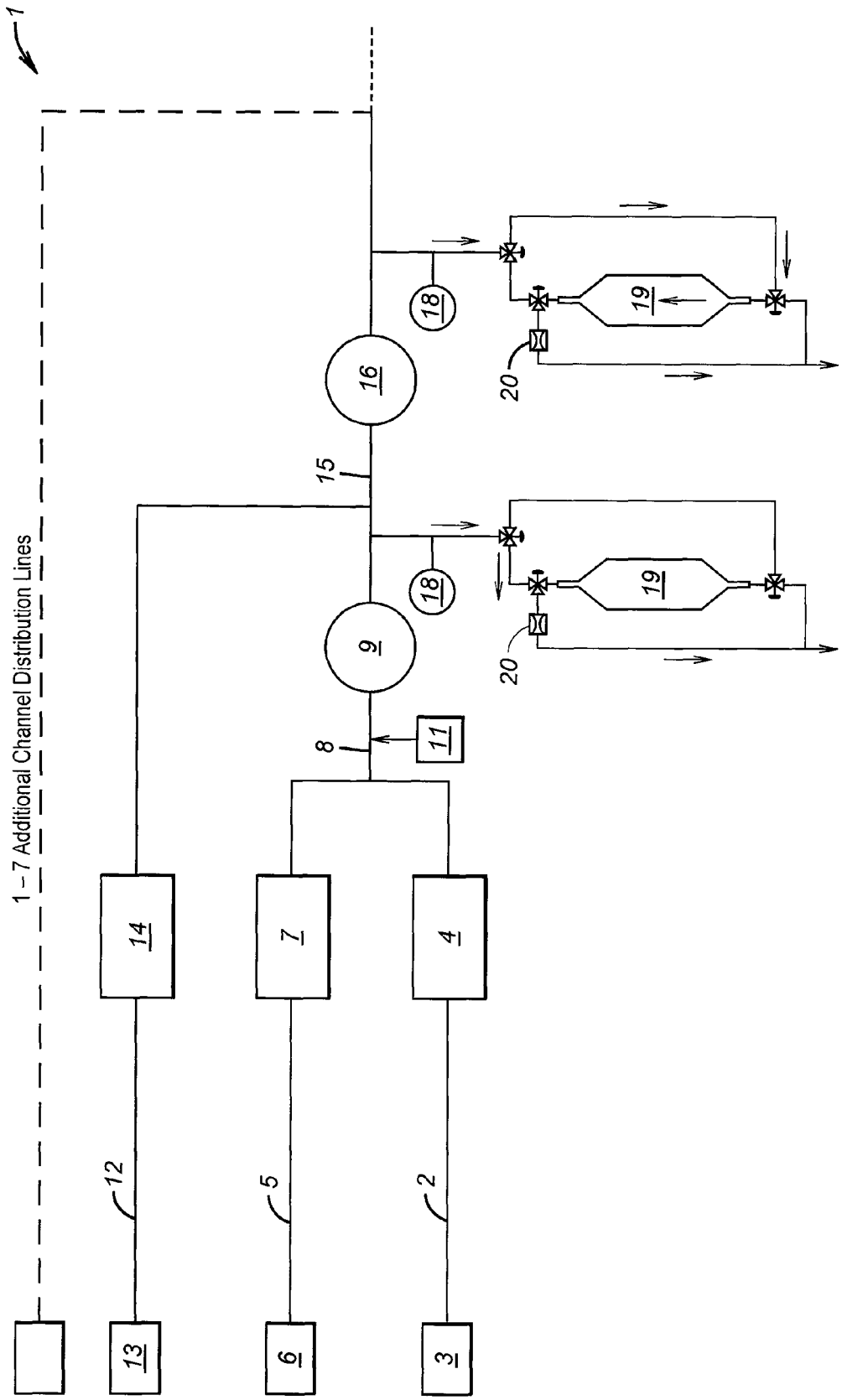
FIG. 1B provides a schematic of the first process embodiment.

In the first process embodiment of the present invention (which is applicable to closed systems) as shown in FIG. 1B, one or more concentration sensors as described hereinbefore of a liquid distribution system (1) as described hereinbefore are checked and calibrated using a flow calibration process. In one alternative, the process is carried out in a liquid distribution system (1) that has a first chemical distribution line (2) that includes a first chemical supply source (3) that houses a first chemical, and a first flow control device (4); a second chemical distribution line (5) that includes a second chemical supply source (6) that houses a second chemical that differs from the first chemical, and a second flow control device (7), the second chemical distribution line (5) coming together with the first chemical distribution line (2) to form a first blended chemical distribution line (8); and a first concentration sensor (9) disposed along the first blended chemical distribution line (8) downstream from where the second chemical distribution line (5) comes together with the first chemical distribution line (2) to form the first blended chemical distribution line (8).

In this first process embodiment, a baseline fluid is allowed to flow through the first concentration sensor (9) in order to establish a baseline calibration reading for the first concentration sensor (9). The baseline fluid may be provided either through one of the chemical distribution lines or through an alternative line (11) specifically included for the baseline fluid. When the baseline fluid is provided through one of the chemical distribution lines, this may be accomplished in one of several manners. First, one or both of the chemical distribution lines may be connected to their associated chemical supply source and a source of baseline fluid using a three way valve thereby allowing for the injection of baseline fluid when the valve is turned in one position and the injection of the associated chemical from the chemical supply source when the valve is in another position. The valve would be set to the position to allow for the baseline fluid to flow, this flow being assisted by the flow control device which would regulate the flow of baseline fluid from the source along the chemical distribution line and through the first concentration sensor where a baseline calibration reading would be established. While the baseline fluid may be flowed through each of the two chemical distribution lines, this is not necessary as the purpose is simply to run a sample of the baseline fluid through the first concentration sensor. Alternatively, the baseline fluid may also function as one of the chemicals stored in the chemical supply source. In this particular case, the baseline fluid would also be one of the chemicals used such as when the chemical is for example deionized water. Furthermore, in this case, the deionized water from either the first chemical supply source or the second chemical supply source would be allowed to flow through the first concentration sensor, assisted by the flow control device positioned on each chemical distribution line. Once the baseline fluid flows through the concentration sensor, a baseline calibration reading is obtained. In a final alternative embodiment, the chemical supply source is replaced with a source of baseline fluid to allow for the injection of the baseline fluid and then the baseline fluid replaced with the chemical supply source (changing out cylinders/tanks). In this alternative, the chemical supply source of one of the chemical distribution lines would be disconnected and attached to the baseline fluid source. The flow control device would then allow for the flow of the baseline fluid through the chemical distribution line and through the concentration sensor. Once the baseline fluid flows through the concentration sensor and a baseline calibration reading is taken, the source of baseline fluid is then detached and the chemical supply source is reattached to the chemical distribution line. This last alternative is a less attractive option since it involves additional down time for the system and increases the possibility of contamination. A still further embodiment involves using an alternative line dedicated specifically to the baseline fluid. This alternative line is an attractive option since it allows for the injection of the baseline fluid at a point near the first concentration sensor (9) thereby eliminating any issues that might arise with regard to the injection of the baseline fluid at other sites along the chemical distribution lines. As noted previously, the baseline fluid may be any fluid which allows for the establishment of a baseline calibration reading for the concentration sensor. In this first process embodiment, the baseline fluid is typically selected from one or more of inorganic compounds such as deionized water, gas such as nitrogen gas or air, organic solvents such as ethylene glycol or toluene, and other types of organic solvents which would be considered as inert for the purposes of this invention, with deionized water being the most preferred.

The next step of the present process embodiment involves calibrating the first flow control device (4) located on the first chemical distribution line (2) and the second flow control device (7) located on the second chemical distribution line (5) in order to achieve an exact flow rate for each of the flow control devices. While the flow control devices of the present invention may be calibrated by any of the methods know in the art, preferably the method utilized is the method disclosed in co-pending U.S. patent application Ser. No. 11/932,635, filed Oct. 31, 2007, incorporated herein in its entirety by reference. More specifically, the method for calibrating a flow control device in a closed system comprises further providing the liquid distribution system (1) utilized in the present invention which includes a flow control device with a pressure sensor (18), a calibration vessel (19), and an adjustable orifice (20), the adjustable orifice (20) being located upstream from the calibration vessel (19) and the pressure sensor (18) being located upstream from the adjustable orifice (20). When calibrating the flow control device, a fluid flows through the liquid distribution system (1), and the flow of the fluid is measured with the flow control device to determine a first flow rate. The fluid flow is then diverted into the calibration vessel (19), which is of a known volume and substantially empty. An indication is received when the calibration vessel is full. This indication comprises registering a change in pressure of the fluid in the liquid distribution system (1), as measured by the pressure sensor (18). The change in pressure is caused by the fluid flowing out of the calibration vessel (19) and through the orifice (20). The time to fill the calibration vessel is measured, and a second flow rate is determined based upon the time required to fill the known volume of the calibration vessel (19).

Once the flow control devices have been calibrated, a target flow rate is set for each of the first flow control device (4) and the second flow control device (7). The target flow rate may be any rate within which the flow control devices would normally run. For example, the target flow rate for one flow control device may be set at 50 milliliters/minute while the second flow control device (7) may be set at 100 milliliters/minute. After the target flow rates are set, the first chemical from the first chemical supply source (3) is allowed to flow along the first chemical distribution line (2) and the second chemical from the second chemical supply source (6) is allowed to flow along the second chemical distribution line (5). The two chemical distribution lines (2, 5) then come together to form a first chemical blend that flows along the first chemical blend distribution line (8). As discussed hereinbefore, the ratio of the blend depends upon the flow rates chosen with regard to each of the flow control devices.

In the next step, the first chemical blend is passed through the first chemical blend distribution line and through the first concentration sensor (9). As the first chemical blend passes through the first concentration sensor (9), a concentration sensor value for the first chemical blend is taken (as a reading or response of the first concentration sensor (9) to the chemical blend). This concentration sensor value for the first chemical blend is compared to a known concentration sensor value of the chemical blend, the known concentration sensor value for the chemical blend having been previously determined using a model specifically established for the chemical blend. The comparison may either be done manually using established curves (models) to establish the known sensor concentration or it may be done in an automated fashion utilizing a programmable logic controller (not shown) which is programmed with established curves (models) that provide the known concentration sensor value or response for the particular chemical blend. Such models can be established individually or may be referenced from established models that are known in the art. In order to establish the models individually, three steps are involved. The first step involves preparing a mixture of the chemical blend with the desired concentration at the desired temperature. By way of a non-limiting example, the chemical blend mixture could comprise sulfuric acid diluted with deionized water. For instance, with regard to this example of sulfuric acid diluted with deionized water, the concentration of samples including 5%, 15%, 25%, 35%, 45%, and 55% of sulfuric acid could be used at varying temperatures 18° C., 25° C., 50° C. and 75° C. in order to give the desired curves which constitute the model to be used. More specifically, one curve would be developed by establishing concentration values for each of these blends at 18° C., another at 25° C., another at 50° C. and another at 75° C. Note that the temperature for the establishing the curves for each model will depend upon the exact chemicals used. The second step involves measuring the concentration sensor value (response) for each of the mixtures prepared in order to establish the corresponding curves. The final step involves refining the data to obtain an equation that models the mixtures behavior. Note that there are various commercially available software programs to plot the obtained curves. The more mixtures that are tested, the more accurate the established curves will be. The process of the present invention will typically be carried out at a temperature that ranges from about 15° C. to about 100° C., with the preferred range being from about 25° C. to about 85° C.

Based on the comparison of the obtained concentration sensor value to the known concentration sensor value as established with the models, the reading (concentration sensor value) may be adjusted accordingly (calibrated) if necessary. The reading of the concentration sensor can be adjusted in a variety of manners including manually or through the use of a programmable logic controller. With regard to the programmable logic controller, the control box of the programmable logic controller will collect and treat the data from the different concentration sensors and adjust the concentration sensor value as needed in order to correspond to the specified concentration.

In addition, the first process embodiment may also include a third chemical distribution line (12) which includes a third chemical supply source (13) that houses a third chemical that differs from the first and second chemical and a third flow control device (14), the third chemical distribution line (12) coming together with the first blended chemical distribution line (8) downstream from the first concentration sensor (9) to form a second blended chemical distribution line (15). This second blended chemical distribution line (15) has disposed thereon a second concentration sensor (16). The second concentration sensor (16) may be calibrated in the same manner as the first concentration sensor (9) by simply repeating the steps, taking into account the additional chemical distribution line. More specifically, a baseline fluid, typically the same as used with regard to the first concentration sensor (9), is flowed through the second concentration sensor (16) via the first, second or third chemical distribution lines (2, 5, 12) or an alternative line (11) specifically for the baseline fluid in order to establish a baseline calibration reading for the second concentration sensor (16). Note that the baseline fluid utilized may come from a separate source (by way of the third chemical distribution line (12) or an alternative line (11) specifically for the second concentration sensor (16)) or more likely due to costs restraints, it will come from the same source as utilized with regard to the first concentration source (either the first or second chemical distribution lines (5) or the alternative line associated with the first concentration sensor (9)). In the next step, at least two of the flow control devices selected from the first flow control device (4), the second flow control device (7) and the third flow control device (14) are calibrated. Once the two or more flow control devices are calibrated, a target flow rate is set for each of the flow control devices calibrated. Next, the chemicals for the chemical distribution lines on which the calibrated flow control devices are located are allowed to flow along their respective chemical distribution lines and to come together to form a resulting chemical blend that flows along the chemical blend distribution line. The resulting chemical blend is passed along the chemical blend distribution line and through the second concentration sensor (16) in order to obtain a concentration sensor value for the resulting chemical blend. Once this concentration sensor value is obtained, it is compared to a known concentration sensor value determined using a model established for the chemical blend as discussed hereinbefore either manually or using a programmable logic controller. Based on this comparison, if necessary, the value of the concentration sensor is adjusted, once again either manually or using a programmable logic controller.

While the above process is directed to one embodiment with two chemical distribution lines and another embodiment with three chemical distribution lines, the process can be utilized with a liquid distribution system having up to ten chemical distribution lines. Accordingly, it is possible to have a total of ten different chemicals with each chemical having its own associated chemical distribution line to allow for the blending of any number of different chemical blends to be used in downstream processes. With regard to each additional chemical distribution line, each will include a flow control device and a chemical supply source that houses a chemical that differs from the chemicals utilized in each of the other chemical distribution lines of the process. Each additional chemical distribution line will come together with the preceding blended chemical distribution line downstream from the concentration sensor located on that particular blended chemical distribution line to form an additional blended chemical distribution line. With regard to each additional blended chemical distribution line, an additional concentration sensor will be disposed along this additional blended chemical distribution line. The remaining steps of the process are generally as described hereinbefore. More specifically, the baseline fluid is flowed through each of the concentration sensors via either one or more of the chemical distribution lines or an alternative line specifically for the baseline fluid in order to establish a baseline calibration reading in each successive individual concentration sensors. Next, at least two of the flow control devices from the chemical distribution lines that precede the concentration sensor to be checked and calibrated are calibrated as described hereinbefore. Once the two or more flow control devices are calibrated, a target flow rate is set for each of the flow control devices calibrated. The chemicals for the chemical distribution lines on which the calibrated flow control devices are located are allowed to flow along their respective chemical distribution lines and to come together to form a resulting chemical blend that flows along the chemical blend distribution line. The resulting chemical blend is passed along the chemical blend distribution line and through the second concentration sensor (16) in order to obtain a concentration sensor value for the resulting chemical blend. Once this concentration sensor value is obtained, it is compared to a known concentration sensor value of the chemical blend as established using the models discussed hereinbefore either manually or using a programmable logic controller. Based on this comparison, if necessary, the concentration sensor value is adjusted either manually or using a programmable logic controller. A chemical blend, once formed may also serve as the basis for additional chemical blends. In such a case, the chemical from the chemical supply source on the additional chemical distribution lines is allowed to flow along the chemical distribution line and be introduced into the preceding chemical blend distribution line to form successive additional chemical blends which flow along an additional chemical blend distribution line. Each additional chemical blend is passed along the successive chemical blend distribution line and through the concentration sensor associated with that particular chemical blend distribution line in order to obtain a concentration sensor value for the that particular chemical blend. Comparisons of values obtained are made with the known values of the particular chemical blends as described hereinbefore. In a still alternative embodiment of this first process embodiment, additional concentration sensors may simply be compared to an already checked and calibrated concentration sensor to determine if the concentration sensor needs to be adjusted (calibrated).

The process of the present invention may also be carried out using an additional concentration sensor located downstream from the each of the concentration sensors positioned along each of the chemical blend distribution lines. In addition, in the preferred embodiment of the present process embodiment, the concentration sensors used are conductivity sensors.

The advantage to this process is that it allows for the calibration of both the flow control devices and the concentration sensors at the same time.

Second Process Embodiment

In the second process embodiment of the present invention which is applicable to closed systems and is depicted in FIG. 1C, one or more concentration sensors as described hereinbefore of a liquid distribution system (1) as described hereinbefore are checked and calibrated using calibration solutions.

The second process embodiment is also carried out in a liquid distribution system (1) that has a first chemical distribution line (2) that includes a first flow control device (4) and a first chemical supply source (3) that houses a first chemical; a second chemical distribution line (5) that includes a second flow control device and a second chemical supply source (6) that houses a second chemical that differs from the first chemical, the second chemical distribution line (5) coming together with the first chemical distribution line (2) to form a first blended chemical distribution line (8); and a first concentration sensor (9) disposed along the first blended chemical distribution line (8) downstream from where the second chemical distribution line (5) comes together with the first chemical distribution line (2) to form the first blended chemical distribution line (8).

In the same manner as described with regard to the first process embodiment, a baseline fluid is allowed to flow through the first concentration sensor (9) in order to establish a baseline calibration reading for the first concentration sensor (9). The baseline fluid may be provided either through one of the chemical distribution lines (2, 5) or through an alternative line (1) specifically included for the baseline fluid in one of the same manners as discussed hereinbefore. The baseline fluid may be any fluid which allows for the establishment of a baseline calibration value reading for the concentration sensor. With regard to this particular process embodiment, the baseline fluid is typically selected from one or more of inorganic compounds such as deionized water, gas such as nitrogen gas or air, organic solvents such as ethylene glycol or toluene, and other types of organic solvents which would be considered as inert for the purposes of this invention and may also be selected from the calibration fluid to be utilized.

The next step in the second process embodiment involves flowing a calibration solution having a known sensor response concentration value through the first concentration sensor (9) by means of either the first or second chemical distribution lines (2, 5) or an alternative line (11) designed specifically for the injection of the baseline fluid into the first concentration sensor (9) in order to obtain a concentration sensor value for the first concentration sensor (9). The calibration solution utilized may be one of the chemicals supplied by the chemical supply source (3, 6) or any commercially available calibration solution that is known for the calibration of sensors such as the one utilized in the present invention. More specifically, by way of example, when the sensor is a conductivity sensor, if one of the chemicals from the chemical supply sources is sulfuric acid, this sulfuric acid may be used to calibrate the sensor or the calibration fluid used may be one or more of the commercially available calibration fluids of the type that are supplied by Amber Science Corp.

This concentration sensor value for the first chemical blend is compared to a known concentration sensor value of the chemical blend as determined using a model established for the chemical blend as described hereinbefore with regard to the first process embodiment. The comparison may either be done manually using established curves (models) to establish the known sensor concentration or it may be done in an automated fashion utilizing a programmable logic controller (not shown) which is programmed with established curves (models) that provide the known concentration sensor value or response for the particular chemical blend. As previously noted, such curves can be established individually or may be referenced from established curves that are known in the art. In order to establish the curves individually, three steps are involved. The first step involves preparing a mixture of the chemical blend with the desired concentration at the desired temperature. The second step involves measuring the concentration sensor value (response) for each of the mixtures prepared in order to establish the corresponding curves. The final step involves refining the data to obtain an equation that models the mixtures behavior. The process of the present invention will typically be carried out at a temperature that ranges from about 15° C. to about 100° C., with the preferred range being from about 25° C. to about 85° C.

Based on the comparison of the obtained concentration sensor value to the known concentration sensor value as established with the models, the value of the concentration sensor may be adjusted, if necessary. The concentration sensor can be adjusted in a variety of manners as discussed with regard to the first process embodiment, including manually or by a program logic controller.

With regard to this particular configuration of the second process embodiment, in those instances where the calibration solution utilized differs in composition from the first or second chemicals, the process will further comprise additional steps of flushing the entire system before use. More specifically, the flushing would include flushing the first chemical distribution line (2) with the first chemical, flushing the second chemical distribution line (5) with the second chemical, and flushing the first blended chemical distribution line (8) with a blend of the first chemical and the second chemical. This added precaution prevents the contamination of any downstream process with the calibration fluid.

In addition, as with the first process embodiment, the second process embodiment may also include a third chemical distribution line (12) which includes a third chemical supply source (13) that houses a third chemical that differs from the first and second chemical, and a third flow control device (14), the third chemical distribution line (12) coming together with the first blended chemical distribution line (8) downstream from the first concentration sensor (9) to form a second blended chemical distribution line (15). This second blended chemical distribution line (15) has disposed thereon a second concentration sensor (16). The second concentration sensor (16) may be calibrated in the same manner as the first concentration sensor (9) by simply repeating the steps with regard to the second concentration sensor (16). More specifically, a baseline fluid, typically the same as used with regard to the first concentration sensor (9), is flowed through the second concentration sensor (16) via the first, second or third chemical distribution lines (2, 5, or 12) or an alternative line (11) specifically for the baseline fluid in order to establish a baseline calibration reading for the second concentration sensor (16). Note that the baseline fluid utilized may come from a separate source (by way of the third chemical distribution line (12) or an additional alternative line (not shown) specifically for the second concentration sensor (16)) or more likely due to costs restraints, it will come from the same source as utilized with regard to the first concentration sensor (either the first or second chemical distribution line (2, 5) or the alternative line associated with the first concentration sensor (9)). The next step involves flowing a calibration solution as described hereinbefore having a known sensor response concentration value through the second concentration sensor (16) by means of either the first, second or third chemical distribution lines (2, 5, or 12) or an alternative line (11) designed specifically for the injection of the baseline fluid into the concentration sensor in order to obtain a concentration sensor value for the first concentration sensor (9). Once the concentration sensor value for the second concentration sensor (16) is obtained, this value is compared to the known concentration sensor value of the calibration fluid (as established by models as discussed hereinbefore with regard to the system having two chemical distribution lines). Based on this comparison, the first concentration sensor (9) is adjusted if necessary either manually or using a programmable logic controller. As with the prior configuration of the second process embodiment, in those instances where the calibration solution utilized differs in composition from the chemicals utilized (the first, second or third chemicals), the process will further comprise additional steps of flushing the entire system before use.

While the above process is directed to one embodiment with two chemical distribution lines and another embodiment with three chemical distribution lines, the process can be utilized with a liquid distribution system (1) having up to ten chemical distribution lines as described hereinbefore. The steps for checking and calibrating are the same as noted with regard to the embodiment with three chemical distribution lines. In a still alternative embodiment of this first process embodiment, the second concentration sensor may simply be compared to an already checked and calibrated first concentration sensor (9) to determine if the second concentration sensor needs to be calibrated. Once this comparison is made, if the second concentration sensor needs to be calibrated, the concentration value of the second concentration sensor can be adjusted either manually or using a programmable logic controller.

The process of the present invention may also be carried out using an additional concentration sensor located downstream from the each of the concentration sensors positioned along each of the chemical blend distribution lines. In addition, in the preferred embodiment of the present process, the concentration sensors are conductivity sensors.

The advantage of this process embodiment is that it is very simple to utilize.

In some cases, the concentration sensor value presents a local minimum, maximum or inflection point for a specific calibration solution that is diluted with the baseline fluid. As used herein with regard to this particular embodiment, the calibration solution can be a chemical which has a property measurement that has a minimum, maximum or inflection point in respect to the concentration change. In this case, the checking and calibration can be performed by adjusting the flow ratio between the calibration solution and the baseline fluid such that the concentration reads the minimum, maximum or inflection point value. Based on the model established, the difference between the reading and the known concentration sensor response defines whether or not the concentration sensor needs to be calibrated. In a preferred embodiment, a calibration solution is diluted out using deionized water which is added to the calibration solution at different flow rates in order to establish the plateau (the minimum, maximum or inflection point values) which is then compared to the plateau established in a model of the chemical blend. Based on this comparison, the value of the concentration sensor is adjusted if necessary (the value obtained is adjusted to reflect the value in the model either manually or using the programmable logic controller which will automatically adjust the readings). The process can be used to calibrate one or more concentration sensors of a liquid distribution system having anywhere from two to ten chemical distribution lines. While any number of lines can be used, preferably only two chemical distribution lines at a time will be utilized. In the preferred embodiment, a baseline fluid is flowed through the concentration sensor to be checked and calibrated via the first chemical distribution line or the second chemical distribution line or an alternative line specifically for the baseline fluid into the first concentration sensor in order to establish a baseline calibration value in the first concentration sensor. After this baseline reading is established, a flow rate is set for each of the flow control devices located along the respective chemical distribution lines. The flow rate may be any rate within which the flow control devices would normally run. While the calibration solution may be any chemical which has a property measurement that has a minimum, maximum or inflection point in respect to the concentration change, in the preferred embodiment, the calibration solution is selected from ammonia, sulfuric acid or hydrochloric acid. The calibration solution utilized is allowed to flow through the first or second chemical distribution line at the designated flow rate with the aid of the flow control device located along that particular chemical distribution line. Deionized water is then allowed to flow through the remaining chemical distribution line at the designated flow rate. The calibration solution and deionized water, each flowing along their designated chemical distribution lines, comes together to form a first calibration blend that flows along the first chemical blend distribution line and through the first concentration sensor. As the first calibration blend flows through the first concentration sensor, a concentration sensor value is obtained for the first concentration sensor. The obtaining of the minimum, maximum or inflection point can be accomplished by holding the flow rate of the calibration solution steady while at the same time steadily adjusting the flow rate of the deionized water. At each adjustment, it is also necessary to measure the concentration sensor value for the first concentration sensor at these varying flow rates until the minimum, maximum or inflection point values are clearly established. Once the minimum, maximum or inflection point is established, the known concentration sensor values of the calibration fluid as established by a model of the chemical blend is compared with the concentration sensor values obtained for the first concentration sensor either manually or using a programmable logic controller. Based on the comparisons of these, the value of the concentration sensor is adjusted either manually or using the programmable logic controller, if necessary. As in the other embodiments of the second process embodiment, if the calibration solution utilized differs in composition from the first and second chemicals to be utilized in the process downstream, the process will further comprise the additional steps of flushing the first chemical distribution line with the first chemical, flushing the second chemical distribution line with the second chemical, and flushing the first blended chemical distribution line with a blend of the first chemical and the second chemical.

Third Process Embodiment

Figure 1D:
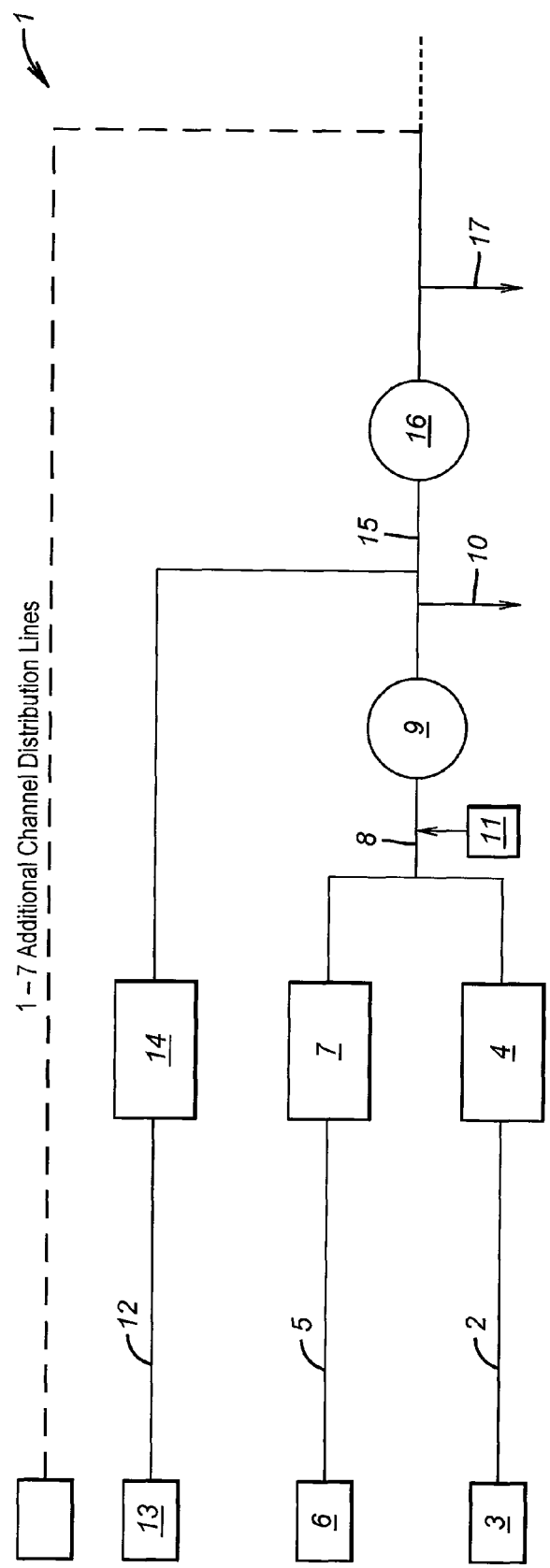
FIG. 1D provides a schematic of the third process embodiment.

The third process embodiment of the present invention, which is applicable to open systems and is depicted in FIG. 1D, allows for the checking and calibration of one or more concentration sensors as described hereinbefore in a liquid distribution system (1) as described hereinbefore by withdrawing a sample of the chemical blend and using either an external concentration sensor that is known to be calibrated correctly or a titration method to determine if calibration of the concentration sensor in the liquid distribution system is necessary. In this particular process embodiment, the liquid distribution system (1) is the same as before with a first chemical distribution line (2), including a first chemical supply source (3) that houses a first chemical, and a first flow control device (4) and a second chemical distribution line (5), including a second chemical supply source (6) that houses a second chemical that differs from the first chemical, and a second flow control device (7). In this particular configuration, the second chemical distribution line (5) comes together with the first chemical distribution line (2) to form a first blended chemical distribution line (8). A first concentration sensor (9) is disposed along this first blended chemical distribution line (8). In this particular embodiment, the system (1) further includes a first sample withdrawal line (10) downstream from the concentration sensor (9) which allows for the removal of a sample of the chemical blend to be utilized in a downstream process. In configurations that will include more than two chemical distribution lines, a sample withdrawal line will be associated with each of the concentration sensors of the liquid distribution system (1). The form of the sample withdrawal line is not critical to the invention provided that it allows for the extraction of a sample of the material that has passed through the specific concentration sensor being checked and calibrated, such as by way of non-limited example a three way valve and drain. While the sample withdrawal line may be located anywhere along the blended chemical distribution line (before of after the concentration sensor, including further downstream provided that the sample is withdrawn prior to the point where another chemical is brought into the distribution line), the preferred placement is just after the concentration sensor that is to be checked and calibrated.

With regard to the third process embodiment, the actual process comprises first flowing a baseline fluid through the first concentration sensor (9) in order to establish a baseline calibration reading for the first concentration sensor (9). The baseline fluid may be provided through one of the chemical distribution lines (2, 5) or through an alternative line (1) specifically included for the baseline fluid in one of the same manners as discussed hereinbefore. As noted previously, the baseline fluid may be any fluid which allows for the establishment of a baseline calibration reading for the concentration sensor, including one or more of inorganic compounds such as deionized water, gas such as nitrogen gas or air, organic solvents such as ethylene glycol or toluene, and other types of organic solvents which would be considered as inert for the purposes of this invention.

Next, the first chemical from the first chemical supply source (3) and the second chemical from the second chemical supply source (6) are allowed to flow (with the assistance of their respective flow control devices (4, 7)) along their respective chemical distribution lines (2, 5). The two chemicals come together to form a first blended chemical which continues to flow along the first chemical blended distribution line (8). This first chemical blend is then passed through the first concentration sensor (9) in order to obtain a concentration sensor value for the first chemical blend. Once this concentration sensor value is obtained, a sample of the first chemical blend is withdrawn from the first blended chemical distribution line (8) utilizing the sample withdrawal line (10) associated with that particular concentration sensor (9).

The sample of the blended chemical that is withdrawn from the first blended chemical distribution line downstream from the concentration sensor (9) being checked and calibrated is then measured using either an external concentration sensor (not shown) that is known to be calibrated properly or a conventional titration method.

When an external concentration sensor is used, this external concentration sensor may be the same type of concentration sensor as that used in the liquid distribution system (1) or it may be a different type of concentration sensor from that used in the liquid distribution system (1). The term type is in reference to the variety of conventional concentration sensors mentioned hereinbefore, for example, refractive index sensors, infrared light absorbent sensors, UV light sensors, conductivity sensors, etc. Preferably, the external concentration sensor is of the same type that is used in the liquid distribution system (1). The external concentration sensor can be calibrated using any known method or can be calibrated by the actual manufacturer. This external concentration sensor, while not being a part of the liquid distribution system (1) may be connected to the programmable logic controller utilized in order to allow the data (reading) from the external concentration sensor to be fed to the particular system utilized for computing the data. Otherwise, the reading can be taken manually. Once the withdrawn sample is passed through the external concentration sensor, an external concentration sensor value for the chemical blend is determined. When the external concentration sensor utilized is the same as that used in the system (1) of the present invention, a direct comparison between the two can be made to determine if the concentration sensor being checked needs to be calibrated. When the concentration sensor is of a different type, then the comparison will be made based on concentrations from established models as described hereinbefore.

Alternatively, the sample that is withdrawn from the first blended concentration distribution line (8) downstream from the concentration sensor (9) being checked and calibrated may be titrated using traditional titration methods. As used herein, the term "titration" refers to the laboratory method used to determine volumetrically the concentration of a substance in solution by adding a standard solution of a known volume and strength until the reaction is complete. One example of such a titration method would be through the use of an indicator and monitoring the change in color (based on a dilution factor). Once this measurement is made, the concentration value, based on the blended chemical, can be determined. This concentration value from the titration process must then be converted using established models to then allow comparison of the concentration sensor value obtained when the same sample was measured in the concentration sensor of the liquid distribution system (1).

As noted with regard to the previous embodiments, the concentration value of the concentration sensor (9) in the liquid distribution system (1) can be adjusted in a variety of manners including manually or through the use of a programmable logic controller. With regard to the programmable logic controller, the control box of the programmable logic controller will collect and treat the data from the liquid distribution system (1) concentration sensor and the external concentration sensor and adjust the liquid distribution system (1) concentration sensor accordingly taking into account the specified concentration and temperature.

The concentration sensor value for the first chemical blend is compared to a known concentration sensor value of the chemical blend (from either the external sensor or by titration) as determined using a model established for the chemical blend as described hereinbefore with regard to the first process embodiment. The comparison may either be done manually using established curves (models) to establish the known sensor concentration or it may be done in an automated fashion utilizing a programmable logic controller (not shown) which is programmed with established curves (models) that provide the known concentration sensor value or response for the particular chemical blend. As previously noted, such curves can be established individually or may be referenced from established curves that are known in the art. As noted previously, in order to establish the curves individually, three steps are involved. The first step involves preparing a mixture of the chemical blend with the desired concentration at the desired temperature. The second step involves measuring the concentration sensor value (response) for each of the mixtures prepared in order to establish the corresponding curves. The final step involves refining the data to obtain an equation that models the mixtures behavior. The process of the present invention will typically be carried out at a temperature that ranges from about 15° C. to about 100° C., with the preferred range being from about 25° C. to about 85° C.

Based on the comparison of the obtained concentration sensor value to the known concentration sensor value as established with the models, the value of the concentration sensor may be adjusted if necessary. The concentration sensor value can be adjusted in a variety of manners as discussed with regard to the first process embodiment, including manually or by a program logic controller.

As with the previous embodiments, the third process embodiment may further comprise a third chemical distribution line (12) that includes a third chemical supply source (13) that houses a third chemical that differs from the first and second chemical and a third flow control device (14). In this system, the third chemical distribution line (12) comes together with the first blended chemical distribution line (8)

downstream from the first concentration sensor (9) to form a second blended chemical distribution line (15). A second concentration sensor (16) is disposed along the second blended chemical distribution line (15). With regard to the specific process utilized in this configuration, the process steps are generally the same as in the system that contains two chemical distribution lines (2, 5). More specifically, a baseline fluid is flowed through the second concentration sensor (16) in order to establish a baseline calibration reading for the second concentration sensor (16). The baseline fluid is selected from the same baseline fluids noted hereinbefore and may be provided through any one or more of the chemical distribution lines or through an alternative line specifically included for the baseline fluid as discussed hereinbefore.

In the next step, the chemicals from at least two of the chemical supply sources (3, 6, or 13) are allowed to flow along their corresponding chemical distribution lines (2, 5, or 12) and come together to form a chemical blend which flows along the noted chemical blend distribution line. For example, the chemical blend may comprise the first chemical and the second chemical which come together to form a chemical blend which passes along the first chemical blend distribution line (8), through the first concentration sensor (9) to the second chemical distribution line (5) and to through the second concentration sensor (16). In an alternative embodiment, the blend may comprise the first chemical and the third chemical, the first chemical flowing along its chemical distribution line (2) to the first blended chemical distribution line (8) through the first concentration sensor (9) and the third chemical flowing along the third chemical distribution line (12) and coming together with the first blended chemical distribution line (8), downstream of the first concentration sensor (9) to form a second blended chemical which then passes along a second blended chemical distribution line (15) to the second concentration sensor (16). This chemical blend is then passed through the second concentration sensor (16) in order to obtain a concentration sensor value for the chemical blend. Once this concentration sensor value for the concentration sensor is obtained, a sample is withdrawn from the second sample withdrawal line (17) associated with the second concentration sensor (16). This sample is then either passed through an external concentration sensor that is known to be correctly calibrated as described hereinbefore or is titrated using a titration method as described hereinbefore to obtain an external concentration sensor concentration value. Once this external concentration sensor concentration value is obtained (using the models as discussed hereinbefore when necessary), it is compared to the concentration sensor value obtained from the concentration sensor (16) that is in the liquid distribution system (1). If necessary, the concentration sensor value of the concentration sensor of the liquid distribution system (1) is then adjusted (calibrated) in the manner as described hereinbefore.

While the above process is directed to one embodiment with two chemical distribution lines and another embodiment with three chemical distribution lines, the process can be utilized with a liquid distribution system (1) having up to ten chemical distribution lines as described hereinbefore. The steps for checking and calibrating are the same as noted with regard to the embodiment with three chemical distribution lines taking into account the additional lines and additional concentration sensors. In a still alternative embodiment of this first process embodiment, the second concentration sensor may simply be compared to an already checked and calibrated first concentration sensor (9) to determine if the concentration sensor needs to be calibrated.

The process of the present invention may also be carried out using an additional concentration sensor located downstream from the each of the concentration sensors positioned along each of the chemical blend distribution lines to serve as backups as described hereinbefore. In addition, in the preferred embodiment of the present process, the concentration sensors are conductivity sensors.

The advantage of this process embodiment is that it provides good precision.

While embodiments of this invention have been shown and described, modifications thereof can be made by one skilled in the art without departing from the spirit or teaching of this invention. The embodiments described herein are exemplary only and not limiting. Many variations and modifications of the composition and method are possible and within the scope of the invention. Accordingly the scope of protection is not limited to the embodiments described herein, but is only limited by the claims which follow, the scope of which shall include all equivalents of the subject matter of the claims.

LISTING OF ELEMENTS

1—liquid distribution system
2—first chemical distribution line
3—first chemical supply source
4—first flow control device
5—second chemical distribution line
6—second chemical supply source
7—second flow control device
8—first blended chemical distribution line
9—first concentration sensor
10—first sample withdrawal line
11—alternative line for baseline fluid
12—third chemical distribution line
13—third chemical supply source
14—third flow control device
15—second blended chemical distribution line
16—second concentration sensor
17—second sample withdrawal line

What is claimed is:

1. A process for calibrating one or more concentration sensors of a liquid distribution system having a first chemical distribution line, including a first chemical supply source that houses a first chemical and a first flow control device, a second chemical distribution line, including a second chemical supply source that houses a second chemical that differs from the first chemical and a second flow control device, the second chemical distribution line coming together with the first chemical distribution line to form a first blended chemical distribution line, and a first concentration sensor disposed along the first blended chemical distribution line, the process comprising the steps of:

a) flowing a baseline fluid through the first concentration sensor via the first chemical distribution line, the second chemical distribution line or an alternative line specifically for the baseline fluid in order to establish a baseline calibration reading in the first concentration sensor;

b) calibrating the first flow control device located on the first chemical distribution line and the second flow control device located on the second chemical distribution line in order to achieve an exact flow rate for each of the flow control devices;

c) setting a target flow rate for each of the first flow control device and the second flow control device;

d) allowing the first chemical from the first chemical supply source and the second chemical from the second chemical supply source to flow along their associated chemical distribution lines and come together to form a first chemical blend that flows along the first chemical blend distribution line;
e) passing the first chemical blend through the first chemical blend distribution line and through the first concentration sensor in order to obtain a concentration sensor value for the first chemical blend;
f) comparing either manually or using a programmable logic controller the concentration sensor value obtained in step e) to the known concentration sensor value of the chemical blend as established by a model; and
g) based on the comparison of step f), adjusting the value of the concentration sensor if necessary.

2. The process of claim 1, wherein the baseline fluid is selected from one or more inorganic compounds, gases and organic solvents.

3. The process of claim 1, wherein an additional concentration sensor is located downstream from the first concentration sensor.

4. The process of claim 1, wherein the distribution system further includes:
a third chemical distribution line, including a third chemical supply source that houses a third chemical that differs from the first and second chemical and a third flow control device, the third chemical distribution line coming together with the first blended chemical distribution line downstream from said first concentration sensor to form a second blended chemical distribution line and a second concentration sensor disposed along the second blended chemical distribution line; and
the process steps further comprise:
a) calibrating the second concentration sensor by flowing a baseline fluid through the second concentration sensor via either the first, second or third chemical distribution line or an alternative line specifically for the baseline fluid in order to establish a baseline calibration reading in the second concentration sensor;
b) calibrating at least two of the flow control devices selected from the first flow control device, the second flow control device and the third flow control device;
c) setting a target flow rate for each of the flow control devices calibrated in b);
d) allowing the chemicals for the chemical distribution lines on which the calibrated flow control devices are located to flow along their respective chemical distribution lines and to come together to form a resulting chemical blend that flows along the chemical blend distribution line;
e) passing the resulting chemical blend along the chemical blend distribution line and through the second concentration sensor in order to obtain a concentration sensor value for the resulting chemical blend;
f) comparing either manually or using a programmable logic controller the concentration sensor value obtained in step e) to the known concentration sensor value of the chemical blend as established by a model; and
g) based on the comparison of step f), adjusting the value of the concentration sensor if necessary.

5. The process of claim 1, wherein the liquid distribution system further comprises:
one or more additional chemical distribution lines, wherein each additional chemical distribution line includes chemical supply source that houses a chemical that differs from the chemicals utilized in each of the other chemical distribution lines of the process, and a flow control device, and each additional chemical distribution line comes together with the preceding blended chemical distribution line downstream from the concentration sensor located on that particular blended chemical distribution line to form an additional blended chemical distribution line and an additional concentration sensor is disposed along this additional blended chemical distribution line; and
the process steps further include:
a) calibrating one of the concentration sensors by flowing a baseline fluid through the concentration sensor via either one or more of the chemical distribution lines or an alternative line specifically for the baseline fluid in order to establish a baseline calibration reading in the concentration sensor;
b) calibrating at least two of the flow control devices selected from the flow control devices located on the chemical distribution lines;
c) setting a target flow rate for each of the flow control devices calibrated in b);
d) allowing the chemicals for the chemical distribution lines on which the calibrated flow control devices are located to flow along their respective chemical distribution lines and to come together to form a resulting chemical blend that flows along the chemical blend distribution line;
e) passing the resulting chemical blend along the chemical blend distribution line and through the concentration sensor to be checked and calibrated in order to obtain a concentration sensor value for the resulting chemical blend;
f) comparing either manually or using a programmable logic controller the concentration sensor value obtained in step e) to the known concentration sensor value of the chemical blend as established by a model;
g) based on the comparison of step f), adjusting the value of the concentration sensor if necessary; and
h) repeating steps a) to g) for any additional concentration sensors to be checked and calibrated.

6. The process of claim 1, wherein each of the flow control devices is calibrated by:
a) flowing a fluid through the liquid distribution system;
b) measuring the flow of the fluid through the distribution system with the flow control device to determine a first flow rate;
c) diverting the fluid flow into the calibration vessel, wherein the calibration vessel is of a known volume and is initially substantially empty;
d) receiving an indication when the calibration vessel is full, wherein receiving the indication comprises registering, with the pressure sensor, a change of pressure in the liquid distribution system, the pressure change caused by the fluid flowing out of the vessel and through the orifice;
e) measuring the time between diverting the fluid flow and receiving the indication; and
f) determining a second flow rate by based upon the known volume of the calibration vessel and the determined time.

7. The process of claim 1, wherein the concentration sensor is a conductivity sensor.

8. A process for calibrating one or more concentration sensors of a liquid distribution system having a first chemical distribution line, including a first chemical supply source that houses a first chemical, and a first flow control device, a second chemical distribution line, including a second chemical supply source that houses a second chemical that differs from the first chemical and, a second flow control device, the second chemical distribution line coming together with said first chemical distribution line to form a first blended chemical distribution line; and a first concentration sensor disposed along the first blended chemical distribution line, the process comprising the steps of:
- a) flowing a baseline fluid through the first concentration sensor via the first chemical distribution line or the second chemical distribution line or an alternative line specifically for the baseline fluid into the first concentration sensor in order to establish a baseline calibration value in the first concentration sensor;
- b) setting an initial flow rate for each of the first flow control device and the second flow control device and flowing a calibration solution through either the first or second chemical distribution line at the initial flow rate, and deionized water through the remaining chemical distribution line at the initial flow rate, the calibration solution and deionized water coming together to form a first calibration blend that flows along the first chemical blend distribution line and through the first concentration sensor in order to obtain a first concentration sensor value for the first concentration sensor;
- c) holding the flow rate of the calibration solution steady while steadily adjusting the flow rate of the deionized water while at the same time continuing to measure the concentration sensor value for the first concentration sensor at the varying flow rates until a minimum, maximum or inflection point is established;
- d) comparing either manually or using a programmable logic controller the concentration sensor value obtained in step c) to the known concentration sensor value of the chemical blend as established by a model; and
- e) based on the comparisons of step d), adjusting the value of the conductivity sensor if necessary;

with the proviso that if the calibration solution utilized differs in composition from the first and second chemicals, the process will further comprise the additional steps of flushing the first chemical distribution line with the first chemical, flushing the second chemical distribution line with the second chemical, and flushing the first blended chemical distribution line with a blend of the first chemical and the second chemical.

9. The process of claim 8, wherein the liquid distribution system further comprises:

a third chemical distribution line, including a third chemical supply source that houses a third chemical that differs from the first and second chemical and a third flow control device, the third chemical distribution line coming together with the first blended chemical distribution line downstream from the first concentration sensor to form a second blended chemical distribution line and a second concentration sensor disposed along the second blended chemical distribution line; and the process steps further comprising:
- a) flowing a baseline fluid through the first concentration sensor via the first, second or third chemical distribution lines or an alternative line specifically for the baseline fluid in order to establish a baseline calibration value for the first concentration sensor;
- b) allowing at least two of the chemicals from the chemical supply sources to flow along their respective chemical distribution lines and to come together to form a chemical blend that flows along the respective chemical blend distribution line;
- c) passing the chemical blend through the chemical blend distribution line and through the concentration sensor to be checked and calibrated in order to obtain a concentration value for the chemical blend;
- d) withdrawing a sample of the chemical blend after the concentration value of the chemical blend is obtained;
- e) measuring the concentration sensor value of the withdrawn sample using either:
  - i) an external concentration sensor that is known to be properly calibrated and that is the same or different from the concentration sensor used in the liquid distribution system with the proviso that when the external sensors are the same, a direct comparison can be made between the sensor values achieved for both the external concentration sensor and the concentration sensor being checked and calibrated and when the external sensor is different, the concentration sensor value of the external concentration sensor is determined using established models for the chemical blend; or
  - ii) a titration method in which the concentration sensor value of the titration method is determined using established models for the chemical blend;
- f) comparing the concentration sensor value obtained in step c) with the concentration sensor value obtained in step e) and adjusting the value of the first concentration sensor if necessary; and
- g) repeating steps a) to f) for any additional concentration sensors to be checked and calibrated.

10. A process for calibrating one or more concentration sensors of a liquid distribution system having a first chemical distribution line, including a first chemical supply source that houses a first chemical and a first flow control device, a second chemical distribution line, including a second chemical supply source that houses a second chemical that differs from the first chemical and a second flow control device, the second chemical distribution line coming together with the first chemical distribution line to form a first blended chemical distribution line, and a first concentration sensor disposed along the first blended chemical distribution line, the process comprising the steps of:
- a) flowing a baseline fluid through the first concentration sensor via the first chemical distribution line, the second chemical distribution line or an alternative line specifically for the baseline fluid in order to establish a baseline calibration reading in the first concentration sensor;
- b) calibrating the first flow control device located on the first chemical distribution line and the second flow control device located on the second chemical distribution line in order to achieve an exact flow rate for each of the flow control devices;
- c) setting a target flow rate for each of the first flow control device and the second flow control device;
- d) allowing the first chemical from the first chemical supply source and the second chemical from the second chemical supply source to flow along their associated chemical distribution lines and come together to form a first chemical blend that flows along the first chemical blend distribution line;
- e) passing the first chemical blend through the first chemical blend distribution line and through the first concentration sensor in order to obtain a concentration sensor value for the first chemical blend;
- f) comparing either manually or using a programmable logic controller the concentration sensor value obtained in step e) to the known concentration sensor value of the chemical blend as established by a model; and
- g) based on the comparison of step f), adjusting the value of the concentration sensor if necessary, wherein each of the flow control devices is calibrated by:
- a) flowing a fluid through the liquid distribution system;

b) measuring the flow of the fluid through the distribution system with the flow control device to determine a first flow rate;
c) diverting the fluid flow into the calibration vessel, wherein the calibration vessel is of a known volume and is initially substantially empty;
d) receiving an indication when the calibration vessel is full, wherein receiving the indication comprises registering, with the pressure sensor, a change of pressure in the liquid distribution system, the pressure change caused by the fluid flowing out of the vessel and through the orifice;
e) measuring the time between diverting the fluid flow and receiving the indication; and
f) determining a second flow rate by based upon the known volume of the calibration vessel and the determined time.

* * * * *